(12) United States Patent
Addison et al.

(10) Patent No.: US 10,426,695 B2
(45) Date of Patent: Oct. 1, 2019

(54) SYSTEM AND METHOD FOR CARDIOPULMONARY RESUSCITATION

(71) Applicant: COVIDIEN LP, Mansfield, MA (US)

(72) Inventors: Paul S. Addison, Edinburgh (GB); James N. Watson, Dunfermline (GB)

(73) Assignee: COVIDIEN LP, Mansfield, MA (US)

( * ) Notice: Subject to any disclaimer, the term of this patent is extended or adjusted under 35 U.S.C. 154(b) by 333 days.

(21) Appl. No.: 15/259,668

(22) Filed: Sep. 8, 2016

(65) Prior Publication Data
US 2017/0065484 A1 Mar. 9, 2017

Related U.S. Application Data

(60) Provisional application No. 62/215,300, filed on Sep. 8, 2015.

(51) Int. Cl.
*A61H 31/00* (2006.01)
*A61B 5/0205* (2006.01)
(Continued)

(52) U.S. Cl.
CPC .......... *A61H 31/005* (2013.01); *A61B 5/0205* (2013.01); *A61B 5/4848* (2013.01); *A61B 5/7264* (2013.01); *A61N 1/3925* (2013.01); *A61B 5/0261* (2013.01); *A61B 5/0402* (2013.01); *A61B 5/14551* (2013.01); *A61B 5/7282* (2013.01); *A61B 2562/02* (2013.01); *A61H 2201/5043* (2013.01); *A61H 2201/5048* (2013.01); *A61H 2201/5092* (2013.01); *A61H 2230/06* (2013.01); *A61H 2230/207* (2013.01); *A61H 2230/40* (2013.01)

(58) Field of Classification Search
CPC . A61B 5/0205; A61B 5/02416; A61B 5/0402; A61B 5/7264; A61B 5/0261; A61H 31/005; G09B 23/288
See application file for complete search history.

(56) References Cited

U.S. PATENT DOCUMENTS

| 4,960,126 A | 10/1990 | Conlon et al. |
|---|---|---|
| 5,078,136 A | 1/1992 | Stone et al. |

(Continued)

FOREIGN PATENT DOCUMENTS

| CN | 103860180 A | 6/2014 |
|---|---|---|
| EP | 1491175 A1 | 12/2004 |

(Continued)

OTHER PUBLICATIONS

U.S. Appl. No. 62/215,300, filed Sep. 8, 2015, Paul S. Addison.
(Continued)

*Primary Examiner* — Jerry-Daryl Fletcher
(74) *Attorney, Agent, or Firm* — Cantor Colburn LLP

(57) ABSTRACT

A method for determining an efficacy of cardiopulmonary resuscitation (CPR) includes receiving a plethysmography signal from an oximetry sensor and an electrocardiogram (ECG) signal from an ECG sensor at a processor associated with a patient monitor, the oximetry sensor, or the ECG sensor. The method includes determining a first indicator related to the efficacy of CPR based on the plethysmography signal, using the processor. The method also includes determining a second indicator related to the efficacy of CPR based on the ECG signal, using the processor. The method further includes combining the first indicator and the second indicator to determine a combination metric indicative of the efficacy of CPR, using the processor.

19 Claims, 5 Drawing Sheets

(51) Int. Cl.
*A61B 5/026* (2006.01)
*A61B 5/00* (2006.01)
*A61N 1/39* (2006.01)
*A61B 5/0402* (2006.01)
*A61B 5/1455* (2006.01)

(56) References Cited

U.S. PATENT DOCUMENTS

| | | | |
|---|---|---|---|
| 5,099,841 | A | 3/1992 | Heinonen et al. |
| 5,662,105 | A | 9/1997 | Tien |
| 5,853,364 | A | 12/1998 | Baker, Jr. et al. |
| 6,083,172 | A | 7/2000 | Baker, Jr. et al. |
| 6,398,727 | B1 | 6/2002 | Bui et al. |
| 6,411,833 | B1 | 6/2002 | Baker, Jr. et al. |
| 6,574,491 | B2 | 6/2003 | Elghazzawi |
| 6,579,242 | B2 | 6/2003 | Bui et al. |
| 6,830,549 | B2 | 12/2004 | Bui et al. |
| 7,006,865 | B1 | 2/2006 | Cohen et al. |
| 7,112,175 | B2 | 9/2006 | Gopinathan et al. |
| 7,171,269 | B1 | 1/2007 | Addison |
| 7,222,054 | B2 | 5/2007 | Geva |
| 7,373,194 | B2 | 5/2008 | Weber et al. |
| 7,435,222 | B2 | 10/2008 | Gopinathan et al. |
| 7,569,018 | B1 | 8/2009 | Geddes et al. |
| 7,976,472 | B2 | 7/2011 | Kiani |
| 8,100,834 | B2 | 1/2012 | Shuler |
| 8,190,223 | B2 | 5/2012 | Al-Ali et al. |
| 8,224,411 | B2 | 7/2012 | Al-Ali et al. |
| 8,983,588 | B2 | 3/2015 | Addison |
| 9,155,493 | B2 | 10/2015 | Addison et al. |
| 2003/0139656 | A1 | 7/2003 | Kiani et al. |
| 2004/0064020 | A1 | 4/2004 | Diab et al. |
| 2004/0267324 | A1 | 12/2004 | Geheb et al. |
| 2005/0267346 | A1 | 12/2005 | Faber et al. |
| 2007/0000531 | A1 | 1/2007 | Russo |
| 2007/0270665 | A1 | 11/2007 | Yang et al. |
| 2008/0097176 | A1 | 4/2008 | Music et al. |
| 2008/0097177 | A1 | 4/2008 | Music et al. |
| 2008/0171311 | A1 | 7/2008 | Corey et al. |
| 2008/0228045 | A1 | 9/2008 | Gao et al. |
| 2009/0171257 | A1* | 7/2009 | Centen .............. A61F 5/0118 602/21 |
| 2009/0204162 | A1 | 8/2009 | Addison et al. |
| 2010/0168605 | A1 | 7/2010 | Aarts |
| 2010/0331715 | A1 | 12/2010 | Addison |
| 2011/0270114 | A1 | 11/2011 | Addison |
| 2012/0101349 | A1 | 4/2012 | DelloStritto et al. |
| 2012/0220844 | A1 | 8/2012 | Baker, Jr. |
| 2012/0232365 | A1 | 9/2012 | Ukawa |
| 2013/0225952 | A1 | 8/2013 | Lin et al. |
| 2014/0073875 | A1 | 3/2014 | Pirow et al. |
| 2015/0105636 | A1 | 4/2015 | Hayman et al. |
| 2016/0206504 | A1* | 7/2016 | Giarracco ............ A61H 31/005 |
| 2016/0278674 | A1* | 9/2016 | Lisogurski ............ A61B 5/7203 |

FOREIGN PATENT DOCUMENTS

| | | |
|---|---|---|
| EP | 2198823 A1 | 6/2010 |
| EP | 2502560 A1 | 9/2012 |
| EP | 2700357 A1 | 2/2014 |
| WO | WO00/38569 A1 | 7/2000 |
| WO | WO2004073787 A2 | 9/2004 |
| WO | WO-2006009830 A2 | 1/2006 |
| WO | WO-2006039752 A1 | 4/2006 |
| WO | WO-2010/096396 A1 | 8/2010 |

OTHER PUBLICATIONS

U.S. Appl. No. 62/105,305, filed Jan. 20, 2015, David J. Giarracco.
U.S. Appl. No. 15/000,770, filed Jan. 19, 2016, David J. Giarracco.
U.S. Appl. No. 09/980,770, filed Nov. 1, 2001, Paul Stanley Addison.
U.S. Appl. No. 11/815,933, filed Sep. 24, 2008, Paul Stanley Addison.

Addison, P., et al.; "Evaluating Arrhythmias in ECG Signals Using Wavelet Transforms;" IEEE Engineering in Medicine and Biology Sep./Oct. 2000, 0739-5175, pp. 104-109.
Addison, P.S., et al.; "Finding Coordinated Atrial Activity During Ventricular Fibrillation Using Wavelet Decomposition"; IEEE Engineering in Medicine and Biology 2002, vol. 21, pp. 58-65.
Addison, P.S.; "Wavelet Transforms and the ECG: A Review"; Physiological Measurement 2005, vol. 26, pp. R155-R199.
Barnum, P.T., et al.; "Novel Pulse Oximetry Technology Capable of Reliable Bradycardia Monitoring in the Neonate," Respiratory Care, vol. 42, No. 1, p. 1072 (Nov. 1997).
Box, M.S., et al.; "Shock Outcome Prediction Before and After CPR: A Comparative Study of Manual and Automated Active Compression—Decompression CPR"; Resuscitation 2008, vol. 78, pp. 265-278.
Chen, Liangyou, et al.; "IS respiration-induced variation in the photoplethysmogram associated with major hypovolemia in patients with actue tramatic injuries," Shock, vol. 34, No. 5, pp. 455-460 (2010).
East, Christine E., et al.; "Fetal Oxygen Saturation and Uterine Contractions During Labor," American Journal of Perinatology, vol. 15, No. 6, pp. 345-349 (Jun. 1998).
Endoh, H., et al.; "Prompt Prediction of Successful Defibrillation From 1-s Ventricular Fibrillation Waveform in Patients with Out-of-hospital Sudden Cardiac Arrest"; T. Journal of Anesthesia 2011, vol. 25(1), pp. 34-41.
Gesquiere, Michael J., et al., "Impact of withdrawal of 450 ML of blook on respiration-induced oscillations of the ear plethysmographic waveform," Journal of Clinical Monitoring and Computing (2007) 21:277-282.
Gundersen, K., et al.; "Identifying Approaches to Improve the Accuracy of Shock Outcome Prediction for Out-of-Hospital Cardiac Arrest"; Resuscitation 2008, vol. 76, pp. 279-284.
Gundersen, K.,; "Using ECG-Analysis to Quantify the Effect of Increasing Pre-Shock Pauses in Chest Compressions on the Probability of ROSC"; Resuscitation 2008, pp. S18-S19.
Hall, M., et al.; "Myocardial Substrate in Secondary Ventricular Fibrillation: Insights from Quantitative Waveform Measures"; Secondary VF and Waveform Measures 2011, vol. 15(3), pp. 388-393.
He, M., et al.; "Prediction of Defibrillation Outcome by Ventricular Fibrillation Waveform Analysis: A Clinical Review;" J Clinic Experiment Cardiol 2013, S10, pp. 1-8.
International Search Report and Written Opinion for PCT Application No. PCT/US2016/014069 dated Apr. 26, 2016, 20 pgs.
Johansson, A.; "Neural network for photoplethysmographic respiratory rate monitoring," Medical & Biological Engineering & Computing, vol. 41, pp. 242-248 (2003).
Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.
Matthews, Nora S. et al.; "An evaluation of pulse oximeters in dogs, cats and horses," Veterinary Anaesthesia and Analgesia, vol. 30, pp. 3-14 (2003).
McGrath, S.P., et al.; "Pulse oximeter plethysmographic waveform changes in awake, spontaneously breathing, hypovolemic volunteers," Anesth. Analg. vol. 112 No. 2, pp. 368-374 (2010).
Nakagawa, Y., et al.; "Amplitude Spectral Area: Predicting the Success of Electric Shock Delivered by Defibrillators with Different Waveforms"; Tokai J Exp Clin Med. 2013, vol. 38(2), pp. 71-76.
Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).
Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.
Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

(56) References Cited

OTHER PUBLICATIONS

Seelbach-Gobel, Birgit, et al.; "The prediction of fetal acidosis by means of intrapartum fetal pulse oximetry," Am J. Obstet. Gynecol., vol. 180, No. 1, Part 1, pp. 73-81 (1999).
Shamir, M., et al.; "Pulse oximetry plethysmographic waveform during changes in blood volume," British Journal of Anaesthesia 82(2): 178-81 (1999).
Sherman, L., et al.; "Beta-Blockade Causes a Reduction in the Frequency Spectrum of VF but Improves Resuscitation Outcome: A Potential Limitation of Quantitative Waveform Measures"; Resuscitation 2012, vol. 83, pp. 511-516.
Sherman, L., et al.; "IThe Comparison of 6 Quantitative Waveform Measures in Measuring the Deterioration of Untreated VF"; Journal of Electrocardiology 2011, vol. 44, p. e 12.
Sipgulis, Janis, et al.; "Optical multi-channel sensing of skin blood pulsations," Optical Sensing, Proceedings of SPIE, vol. 5459, pp. 46-53 (2004).
Stiles, M.K., et al.; "Wavelet Based Analysis of Heart-Rate-Dependent ECG Features"; Annals of Noninvasive Electrocardiology 2004, vol. 9(4), pp. 316-322.
Watson, J.N.; "A Novel Wavelet Transform Based Analysis Reveals Hidden Structure in Ventricular Fibrillation"; Resuscitation 2000, vol. 43(2), pp. 121-127.
Watson, J.N., et al.; "Angular Velocity: a new method to improve prediction of ventricular fibrillation duration;" Resuscitation Letter—Published Paper 2004, vol. 62 pp. 124-125.
Watson, J.N., et al.; "Improved Prediction of Defibrillation Success for Out-of-Hospital VF Cardiac Arrest Using Wavelet Transform Methods"; Resuscitation 2004, vol. 63(3), pp. 269-275.
Watson, J.N. et al.; "Wavelet Transform-based Prediction of the Likelihood of Successful Defibrillation for Patients Exhibiting Ventricular Fibrillation"; Measurement Science and Technology 2005, vol. 16, L1-L6.
Watson, J.N., et al.; "Practical Issues in the Evaluation of Methods for the Prediction of Shock Outcome Success in Out-of-hospital Sudden Cardiac Arrest Patients"; Resuscitation 2006, vol. 68, pp. 51-59.
Watson, J.N., et al.; "Wavelet Transform Analysis Predicts Outcome of DC Cardioversion for Atrial Fibrillation Patients"; Computers in Biology and Medicine 2007, vol. 37, pp. 517-523.
Wijshoff, Ralph WC.G.R., et al., "Detection of a spontaneous pulse in phtoplethysmograms during automated cardiopulmonary resuscitation in a porcine model," Resuscitation, vol. 84, No. 11, pp. 1625-1632.
Wijshoff, Ralph WC.G.R., et al., "Photoplethysmography-Based Algorithm for Detection of Cardiogenic Output during Cardiopulmonary Resuscitation," IEEE Transactions on Biomedical Engineering, vol. 62, No. 3; pp. 909-921 (2015).
Wik, L., et al.; "Delaying Defibrillation to Give Basic Cardiopulmonary Resuscitation to Patients With Out-of-Hospital Ventricular Fibrillation;" American Medical Association 2003, vol. 289, No. 11, pp. 1389-1395.
Wu, Dongmei, et al.; "Na*/H* Exchange inhibition delays the onset of hypovolemic circulatory shock in pigs," Shock, vol. 29, No. 4, pp. 519-525 (2008).
Yoon, Gilwon, et al.; Multiple diagnosis based on Photoplethysmography: hematocrit, SpO2, pulse and respiration, Optics in Health Care and Biomedical optics: Diagnostics and Treatment; Proceedings of the SPIE, vol. 4916; pp. 185-188 (2002).

* cited by examiner

SYSTEM AND METHOD FOR CARDIOPULMONARY RESUSCITATION

CROSS-REFERENCE TO RELATED APPLICATION

This application claims priority to and the benefit of Provisional Application No. 62/215,300, entitled "SYSTEM AND METHOD FOR CARDIOPULMONARY RESUSCITATION," filed Sep. 8, 2015, which is incorporated by reference herein in its entirety for all purposes.

BACKGROUND

The present disclosure relates generally to cardiopulmonary resuscitation and, more particularly, to sensors and/or monitors and/or algorithms configured to assist a person in performing cardiopulmonary resuscitation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In many medical emergencies, a person's heart may stop pumping on its own. The person may need emergency resuscitation, such as cardiopulmonary resuscitation (CPR) to sustain the life of the person by manually maintaining intact brain function. Typically, CPR involves manually pumping the chest (i.e., chest compressions) to force blood through the cardiovascular system to organs such as the brain. CPR also involves occasionally blowing oxygenated air (i.e., administered breaths or artificial respiration) into the lungs of the person so that oxygen may be absorbed into the bloodstream. However, the person administering the CPR, whether a trained emergency responder or a person with little training or experience in administering CPR, has little to no feedback as to the effectiveness of the CPR (e.g., quality of chest compressions or applied breaths) being administered. Consequently, the CPR may not be administered as effectively as possible.

BRIEF DESCRIPTION OF THE DRAWINGS

Advantages of the disclosed techniques may become apparent upon reading the following detailed description and upon reference to the drawings in which:

FIG. 4b is a graphical representation of a plethysmography signal over the period of time of FIG. 4a;

FIG. 5b is a graphical representation of a modulus maxima scalogram corresponding to the ECG signal of FIG. 5a;

DETAILED DESCRIPTION OF SPECIFIC EMBODIMENTS

Figure 1:
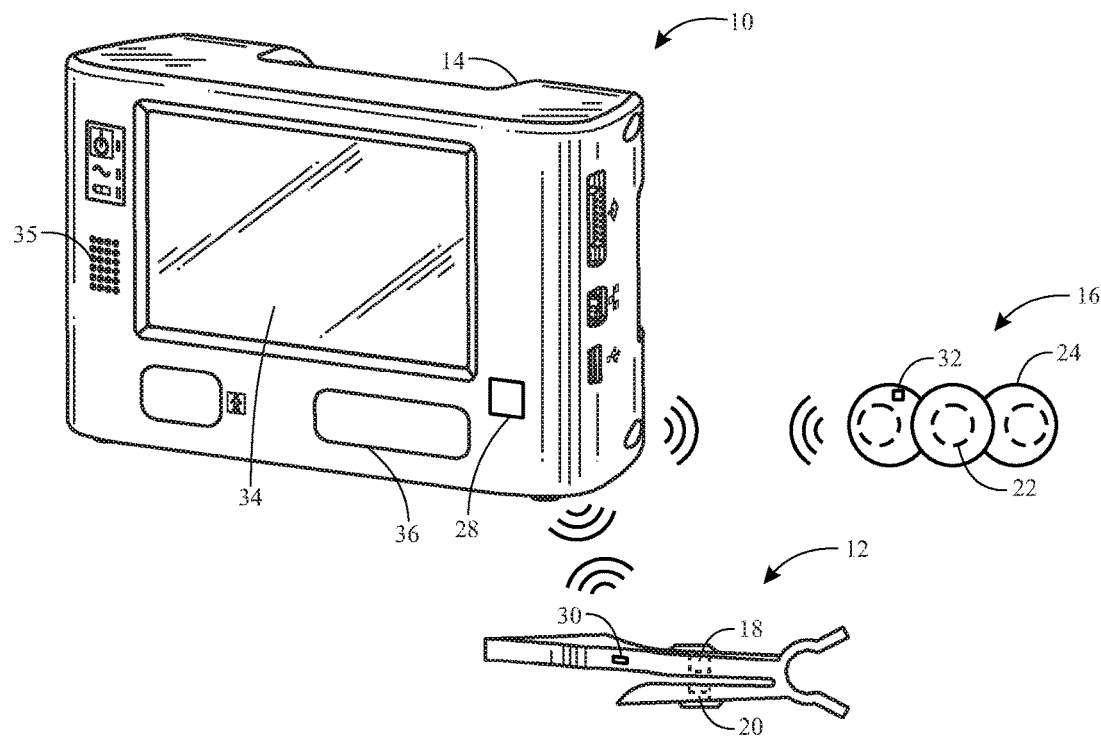
FIG. 1 is a perspective view of an embodiment of a medical monitoring system, in accordance with an aspect of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Also, as used herein, the term "over" or "above" refers to a component location on a sensor that is closer to patient tissue when the sensor is applied to the patient.

The present embodiments relate generally to emergency response systems (e.g., emergency response kits having components described below provided or sold as a single unit for use in an emergency response) that may include one or more sensors and/or a monitor configured to monitor one or more physiological signals (e.g., a plethysmography signal and/or an electrocardiogram (ECG) signal) of a patient (i.e., person receiving emergency resuscitation, such as CPR). In certain embodiments, the system includes an oximetry sensor and/or an ECG sensor (e.g., electrodes). The oximetry sensors described herein may incorporate one or more emitters configured to emit light into a patient at one or more wavelengths and one or more detectors configured to detect a signal representative of reflected or transmitted light received from the patient. This acquired signal may be used to determine any of a variety of physiological characteristics of the patient, such as the level of blood oxygen saturation in an artery of the patient, for example. This signal may be referred to as a plethysmography signal or plethysmograph. This signal typically reflects cardiac pulses in the patient's blood due to contractions of the heart. During CPR, this signal may include non-cardiac pulses (i.e., pulses due to the administration of chest compressions during CPR, rather than to the contraction of the patient's heart). The ECG sensors described herein may incorporate one or more electrodes that are configured to measure electrical potentials generated by the patient's heart, and the ECG signal generated by the electrodes may reflect an underlying myocardial rhythm during CPR.

While guidelines related to performance of CPR exist (e.g., chest compression rate, depth and frequency of breathing, or the like), the presently disclosed systems and methods may provide improved patient outcomes by facilitating optimization or improvement of CPR for the anatomy and physiology of the patient. During cardiac arrest, healthcare providers may attempt cardioversion of ventricular fibrillation (VF) via a defibrillation shock and/or may apply CPR to maintain the viability of the heart and brain until spontaneous circulation can be re-established. Variations in the VF waveform may reflect the health of the myocardium and certain variations in the VF waveform may indicate that a defibrillation shock is likely to lead to the return of spontaneous circulation (e.g., a shockable myocardial rhythm). Additionally, the VF waveform and the health of the myocardium can be improved with the application of CPR. Accordingly, it may be beneficial to monitor and provide reliable feedback regarding the efficacy of CPR and/or a probability of a return of spontaneous circulation upon application of a defibrillation shock. Such embodiments may enable the healthcare provider to provide effective CPR and/or to apply the defibrillation shock when a shockable myocardial rhythm is identified.

Accordingly, in some embodiments disclosed herein, the plethysmography signal and/or the ECG signal may be analyzed to determine the efficacy of CPR being administered to the patient. For example, one or more of an amplitude of non-cardiac (e.g., CPR) pulses in the plethysmography signal, an oxygen saturation ($SpO_2$), a regional oxygen saturation ($rSO_2$), a perfusion index, a characteristic of a baseline of the plethysmography signal, or any combination thereof may be used to determine the efficacy of CPR. Additionally or alternatively, a characteristic measure related to the ECG signal may be used to determine the efficacy of CPR. In some embodiments, the ECG signal may be processed to provide a cardioversion outcome prediction (COP) metric, which may generally quantify a probability of success (i.e., a return of spontaneous circulation) upon application of shock therapy (e.g., a defibrillation shock), and the COP metric may be used to determine the efficacy of CPR.

In some embodiments, the plethysmography signal and/or the ECG signal may additionally or alternatively be analyzed to determine a probability of success upon application of shock therapy. For example, the perfusion index, the characteristic of the baseline of the plethysmography signal, and/or the COP metric may be used to determine the probability of success upon application of shock therapy. The systems and methods disclosed herein may be configured to provide feedback regarding the efficacy of CPR and/or the probability of success upon application of shock therapy to the person administering the CPR (e.g., via a speaker and/or a display).

With the foregoing in mind, FIG. 1 depicts an embodiment of a patient monitoring system 10 that includes a patient monitor 14 that may be used in conjunction with one or more medical sensors, such as an oximetry sensor 12 and/or an ECG sensor 16. The sensors 12, 16 may be reusable, entirely disposable, or include disposable portions. Although only one oximetry sensor 12 and one ECG sensor 16 are shown in FIG. 1, in other embodiments, two, three, four, or more oximetry sensors 12 and/or ECG sensors 16 may be communicatively coupled to the monitor 14. For example, two oximetry sensors 12 may be used for simultaneously monitoring blood oxygen saturation at two different body locations of the patient.

As shown in FIG. 1, the oximetry sensor 12 includes an emitter 18 and a detector 20. Although the depicted oximetry sensor 12 is configured for use on a patient's finger, it should be understood that, in certain embodiments, the oximetry sensor 12 may be adapted for use at other tissue locations. Furthermore, as shown, the ECG sensor 16 includes multiple electrodes 22 coupled to a substrate 24 that is configured to be attached (e.g., adhered) to the patient, although the ECG sensor 16 may have any suitable configuration for obtaining an ECG signal. For example, the ECG sensor 16 may include an implantable device, such as a pacemaker.

The sensors 12, 16 may be wireless sensors and may be configured to communicate wirelessly with the monitor 14. In some embodiments, the monitor 14 includes a wireless transceiver 28 configured to transmit data to and receive data from the sensors 12, 16 (e.g., via a wireless transceiver 30 of the oximetry sensor 12 and/or a wireless transceiver 32 of the ECG sensor 16). The wireless transceivers 30, 32 of the sensors 12, 16 may be configured to establish wireless communication with one another and/or with the wireless transceiver 28 of the monitor 14 using any suitable protocol. By way of example, the wireless transceivers 28, 30, 32 may be configured to communicate using the IEEE 802.15.4 standard, and may communicate, for example, using ZigBee, WirelessHART, or MiWi protocols. Additionally or alternatively, the wireless transceivers 28, 30, 32 may be configured to communicate using the Bluetooth standard or one or more of the IEEE 802.11 standards. In certain embodiments, one or more of the sensors 12, 16 may be integrated with the monitor 14 in a single unit. The integrated monitor could be a standalone unit, configured to be strapped to the patient and in direct view of the operator. Such embodiment would present the advantages of greater mobility and reduced number of parts. In some embodiments, one or more of the sensors 12, 16 may be configured to communicate with the monitor 14 via a wired connection (e.g., via a cable).

The monitor 14 includes a monitor display 34 that may be configured to display information regarding the physiological parameters monitored by the sensors 12, 16, information related to the signals obtained by the sensors 12, 16, information about the system 10, and/or alarm indications, for example. In addition, the monitor display 34 may be configured to communicate information related to the efficacy of the CPR being administered to the patient and/or information related to a probability of success upon application of shock therapy. As discussed in more detail below, the monitor display 34 may provide information related to chest compressions (e.g., "alter compressions," "change location of compressions," "compression too light," "compression too hard," "slow down compressions," "speed up compressions," etc.) and/or artificial respiration ("give more breaths" or "give fewer breaths"). This information may relate to altering chest compressions and/or administered breaths, changing a location of the chest compressions, changing the amount of force applied during the chest compressions (e.g., too light, too hard, etc.), and/or the effectiveness of the administered breaths (e.g., an amount, frequency, etc.). In some embodiments, the monitor display 34 may provide information related to administration of a defibrillation shock (e.g., "provide a shock," "do not provide a shock," "proceed to chest compression," etc.). The information may be displayed via text, images, and/or color-coded indicators, for example.

The monitor 14 may also include a speaker 35 to communicate information related to the efficacy of the CPR being administered to the patient and/or information related to the prediction of shock outcome. For example, the speaker 35 may communicate audible instructions (e.g., spoken or voice messages to "change location of compressions," "compression too light," "compression too hard," "slow down compressions," "speed up compressions," "provide a shock," "do not provide a shock," "apply chest compressions," etc.). In addition, the speaker 35 may emit a sound (e.g., beep) to indicate certain instructions, to reflect a detected pulse (e.g., a non-cardiac pulse), to reflect a return of spontaneous circulation, or the like. In some embodiments, a pitch, tone, or other characteristic of the sound may be varied to indicate chest compressions are being administered too fast, too slow, at a correct rate, and/or that a defibrillation shock should be applied. The monitor 14 may include various input components 36 (e.g., input), such as knobs, switches, keys and keypads, buttons, touchscreen, microphone (e.g., to enable spoken prompts or inputs), etc., to provide for operation and configuration of the monitor 14. The input components 36 may enable the inputting and/or adjusting of patient characteristics (e.g., patient age, size, condition, etc.), inputting that the sensors 12, 16 have been applied to the patient, inputting a beginning and/or end of the administration of CPR to the patient (e.g., initiation of a "CPR mode"), and/or inputting and/or adjusting ranges, values, and/or thresholds.

As discussed in more detail below, the monitor 14 also includes a processor that may be used to execute code stored in memory or other suitable computer-readable storage medium or memory circuitry, such as code for implementing various monitoring functionalities. As discussed below, for example, the monitor 14 may be configured to process signals generated by the detector 20 of the oximetry sensor 12 and/or ECG signals generated by the electrodes 22 of the ECG sensor 16 to provide an indication of the efficacy of CPR being administered to the patient and/or to provide a probability of success upon application of shock therapy, thereby facilitating optimization or improvement of CPR for the patient.

Figure 2:
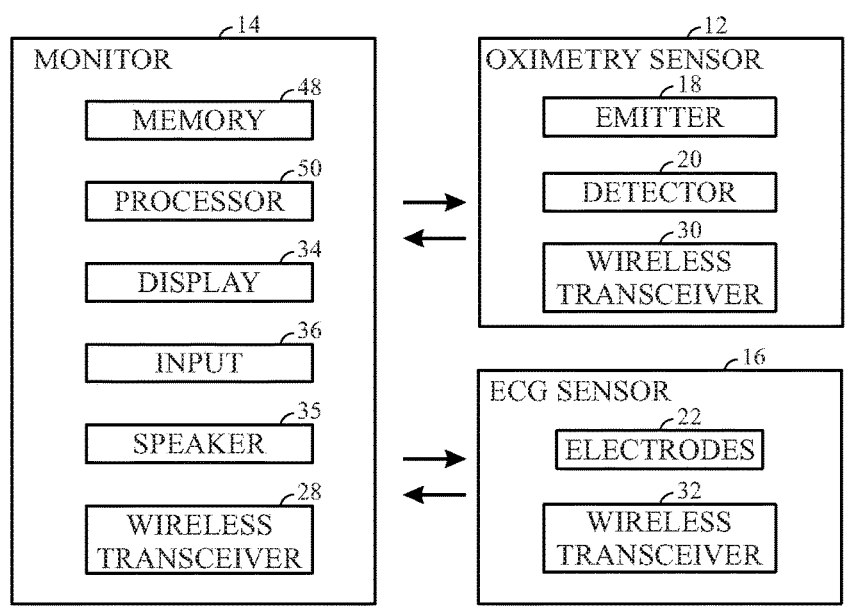
FIG. 2 is a block diagram of the medical monitoring system of FIG. 1, in accordance with an aspect of the present disclosure.

Turning to FIG. 2, a simplified block diagram of the medical system 10 is illustrated in accordance with an embodiment. The oximetry sensor 12 may include optical components in the form of the emitter 18 and the detector 20. The emitter 18 and the detector 20 may be arranged in a reflectance or transmission-type configuration with respect to one another. The emitter 18 may be a light emitting diode, superluminescent light emitting diode, a laser diode, or a vertical cavity surface emitting laser (VCSEL). The emitter 18 and the detector 20 may also include optical fiber sensing elements. Also, the emitter 18 may include two light emitting diodes (LEDs) that are configured to emit at least two wavelengths of light, e.g., red or near infrared light. In one embodiment, the LEDs emit light in the range of 600 nm to about 1000 nm. In a particular embodiment, the one LED is configured to emit light at 730 nm and the other LED is configured to emit light at 810 nm. The emitter 18 may be driven by light drive circuitry of the monitor 14.

In one embodiment, light enters the detector 20 after passing through the tissue of the patient. In another embodiment, light emitted from the emitter 18 may be reflected by elements in the patent's tissue to enter the detector 20. The detector 20 may convert the received light at a given intensity, which may be directly related to the absorbance and/or reflectance of light in the tissue of the patient, into a plethysmography signal. After converting the received light to the plethysmography signal, the detector 20 may send the plethysmography signal to the monitor 14, where signal characteristics may be analyzed and/or physiological characteristics may be calculated based at least in part on the absorption and/or reflection of light by the tissue of the patient.

The ECG sensor 16 may include multiple electrodes 22 that are configured to sense electrical potentials generated by the patient's heart when the ECG sensor 16 is applied to the patient's chest. The electrodes 22 may convert the electrical potentials into an ECG signal. The ECG signal may be provided to the monitor 14, where signal characteristics may be analyzed. In particular, one or more processors 50 of the monitor 14 may process the plethysmography signal and/or the ECG signal to determine the efficacy of CPR being administered to the patient and/or to determine a probability of success upon application of shock therapy, thereby facilitating optimization or improvement of CPR for the patient. As shown, the monitor 14 includes the processor 50, a memory 48, the display 34, the speaker 35, the user input 36, and the wireless transceiver 28. As noted above, the wireless transceivers 30, 32 of the sensors 12, 16 may be configured to establish wireless communication with one another and/or with the wireless transceiver 28 of the monitor 14 using any suitable protocol. In some embodiments, one or more of the sensors 12, 16 or associated cables may be configured to communicate with the monitor 14 via a wired connection (e.g., via a cable). In some embodiments, one or more of the sensors 12, 16 may have any of the components (e.g., the processor 50, the memory 48, the display 34, the speaker 35, the user input 36) discussed above with respect to the monitor 14 and any of the methods disclosed herein may be carried out by the components of one or more of the sensors 12, 16.

In certain embodiments, the processor 50 may be configured to determine one or more first indicators based on the plethysmography signal received from the oximetry sensor 12 and to determine one or more second indicators based on the ECG signal received from the ECG sensor 16. In some embodiments, the first indicator may include an amplitude of a non-cardiac pulse, an oxygen saturation ($SpO_2$), a regional oxygen saturation ($rSO_2$), a perfusion index, a characteristic of a baseline of the plethysmography signal, or any combination thereof, and the second indicator may include a characteristic measure of the ECG signal, a cardioversion outcome prediction (COP) metric, or any combination thereof. The processor 50 may be configured to use the one or more first indicators and/or the one or more second indicators to determine the efficacy of CPR and/or the probability of success upon application of shock therapy.

Figure 3:
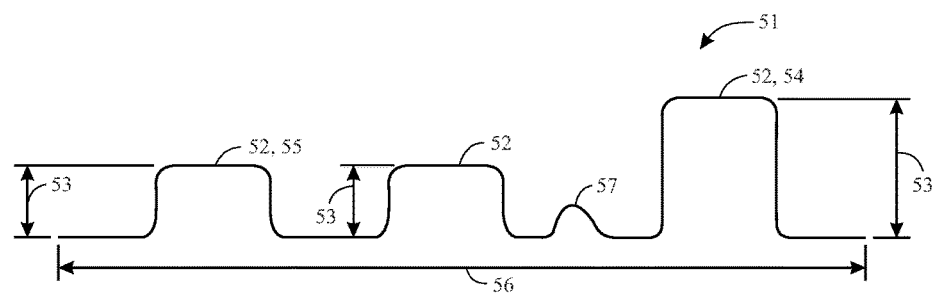
FIG. 3 is a graphical representation of a plethysmography signal during administration of CPR.

With the foregoing in mind, the processor 50 may be configured to determine the efficacy of CPR based at least in part on an amplitude of non-cardiac pulses (i.e., a pleth CPR (PCPR) metric) as disclosed in U.S. Patent Application No. 62/105,305, which is hereby incorporated by reference in its entirety for all purposes. FIG. 3 illustrates a signal 51 obtained from the oximetry sensor 12 during CPR. As shown, the signal 51 includes multiple non-cardiac pulses 52 due to CPR. Each non-cardiac pulse 52 includes a pulse amplitude 53 (i.e., peak to peak amplitude for the pulse 52). The pulse amplitude 53 may be related (e.g., linearly related) to the force applied during the chest compression and/or the effectiveness of the chest compression (e.g., location of the chest compression). For example, a stronger chest compression may result in a larger pulse amplitude 53 (see pulse amplitude 53 for relatively stronger pulse 54 in FIG. 3) relative to the pulse amplitude 53 from a weaker chest compression (see pulse amplitude 53 for relatively weaker pulse 55 in FIG. 3). Similarly, a chest compression administered in the wrong location (e.g., off-center) may result in a smaller pulse amplitude 53 (see pulse amplitude 53 for pulse 55 in FIG. 3) than a pulse amplitude 53 from a chest compression administered in the proper location (see pulse amplitude 53 for pulse 54 in FIG. 3). FIG. 3 also illustrates the pulse rate (i.e., frequency) of the signal 51 (i.e., the number of pulses 52 within a defined period of time 56). Generally the frequency of the detected pulses 52 may be the same as the frequency of the chest compressions administered during the CPR.

In some embodiments, the processor 50 may be configured to apply a pulse qualification algorithm to identify modulations in the plethysmography signal that are due to CPR (e.g., non-cardiac pulses due at least in part to chest compressions applied during CPR, such as non-cardiac pulses 52), and to thereby distinguish such non-cardiac pulses due to CPR from various signal artifacts (e.g., such as modulations 57 due to noise from motion, ambient light, or the like). In certain embodiments, the processor 50 may be configured to determine the amplitude 53 of each of the qualified non-cardiac pulses 52. In some embodiments, the amplitude may be a normalized amplitude normalized by a baseline of the plethysmography signal (e.g., the pulse amplitude may be divided by the baseline level of the signal, providing an AC (alternative or pulsatile) over DC (direct, non-alternative or non-pulsatile) metric).

Additionally or alternatively, in some embodiments, the processor 50 may be configured to determine the patient's oxygen saturation ($SpO_2$) based on the signal 51 (e.g., using one or more algorithms configured to calculate $SpO_2$). In certain embodiments, the oximetry sensor 12 may be adapted to perform regional oximetry and/or an additional oximetry sensor 12 that is configured to perform regional oximetry may be provided within the system 10. In regional oximetry, by comparing the relative intensities of light received at two or more detectors, it is possible to estimate the blood oxygen saturation of hemoglobin in a region of a body. For example, a regional oximeter may include a sensor to be placed on a patient's forehead and may be used to calculate the oxygen saturation of a patient's blood within the venous, arterial, and capillary systems of a region underlying the patient's forehead (e.g., in the cerebral cortex). In such cases, the oximetry sensor 12 may include the emitter 18 and two detectors 20: one detector that is relatively "close" to the emitter 16 and another detector that is relatively "far" from the emitter 18. Light intensity of one or more wavelengths may be received at both the "close" and the "far" detectors, and thus, one detector may receive a first portion of light and the other detector may receive a second portion of light. Each of the detectors 20 may generate signals indicative of their respective portions of light. For example, the resulting signals may be compared to arrive at a regional saturation value that pertains to additional tissue through which the light received at the "far" detector passed when it was transmitted through a region of a patient. Surface data from the skin and skull is subtracted out to produce a regional oxygen saturation ($rSO_2$) value for deeper tissues. The processor 50 may be configured to determine the efficacy of the CPR based at least in part on the $SpO_2$ and/or $rSO_2$, as discussed in more detail below.

In some embodiments, the processor 50 may be configured to determine a perfusion index based on the plethysmography signal. The perfusion index may be generally indicative of a pulse strength and blood flow (e.g., blood flow rate) at the monitoring site, which is expected to increase (e.g., as compared to an initial value at the onset of ventricular fibrillation and/or at the onset of CPR) and/or remain above a minimum value during effective CPR and/or as the state of myocardium improves. The perfusion index may be a numerical indicator calculated based on the normalized amplitude of any suitable pulsatile waveform (e.g., cardiac pulses or non-cardiac pulses) in the plethysmography signal (e.g., signal 51). In particular, the perfusion index may be calculated as a ratio of an AC (pulsatile) component to a DC (non-pulsatile) component of the plethysmography signal. In some embodiments, the processor 50 may be configured to determine the efficacy of the CPR based at least in part on the perfusion index.

Figure 4A:
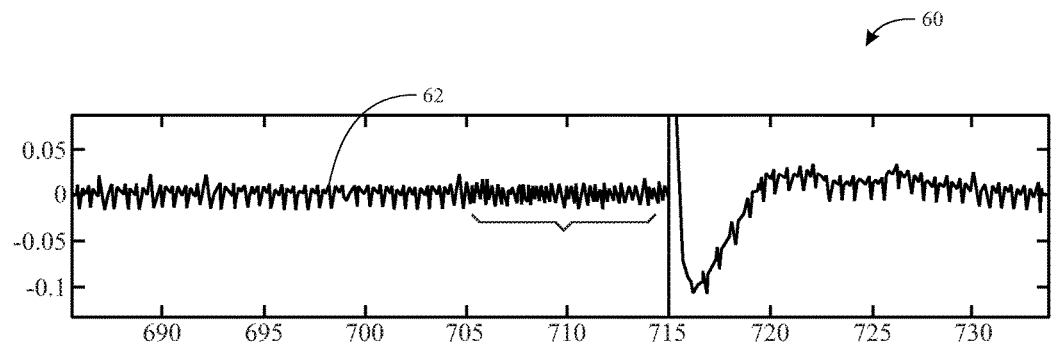
FIG. 4a is a graphical representation of an electrocardiogram (ECG) signal over a period of time.
Figure 4B:
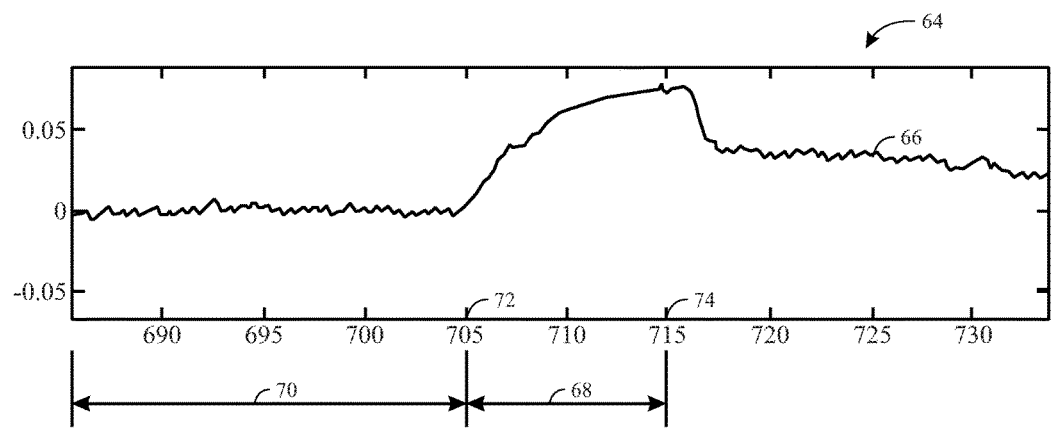

FIGS. 4a and 4b are examples of an ECG signal and a plethysmography signal, respectively, over a period of time during which a subject transitions from normal cardiac function to ventricular fibrillation and subsequently experiences a defibrillation shock. In particular, FIG. 4a is an example of a graph 60 of an ECG signal 62 over a period of time, and FIG. 4b is an example of a graph 64 of a baseline 66 of a plethysmography signal over the period of time. As shown, the subject initially demonstrates a period of normal cardiac function 70. When the patient transitions into a period of ventricular fibrillation 68 at a first time 72, the baseline 66 of the plethysmography signal changes (e.g., shifts). The shift may be due to a rapid loss of blood pressure and a corresponding reduction in blood flow at the monitoring site following cardiac arrest, which causes a decrease in absorption of light and an increase in the baseline 66. When the patient receives a defibrillation shock at a second time 74, the blood flow begins to return (e.g., trend) toward levels observed during the period of normal cardiac function 70, which causes an increase in the absorption of light and a decrease in the baseline 66, as shown. In some embodiments, the processor 50 may be configured to monitor the baseline 66 of the plethysmography signal and to determine one or more characteristics of the baseline 66. The baseline 66 may be generally indicative of blood flow (e.g., blood flow rate) at the monitoring site, which is expected to increase (e.g., as compared to an initial value at the onset of ventricular fibrillation and/or at the onset of CPR) and/or remain above a minimum value during effective CPR and/or as the state of myocardium improves.

In some embodiments, the processor 50 of the monitor 14 may be configured to determine one or more characteristics of the baseline 66 of the plethysmography signal. For example, the processor 50 may determine a percent change in the baseline over a period of time or as compared to the baseline 66 during the period of normal cardiac function 70. In some embodiments, the processor 50 may determine a gradient of the baseline 66 at various times, including during the onset of VF, after the defibrillation shock, or at any other suitable time. In some embodiments, the processor 50 may determine an amplitude of any features (e.g., discrete features or waves) in the baseline 66.

In some embodiments, the baseline 66 may be derived from a red baseline (e.g., generated by the detector 20 in response to detection of wavelengths of light in the red spectrum emitted by a light source of the emitter 18) and/or from an IR baseline (e.g., generated by the detector 20 in response to detection of wavelengths of light in the IR spectrum emitted by a light source of the emitter 18). For example, in some embodiments, the baseline 66 may be derived by averaging the red baseline and the IR baseline, which may reduce noise. In some embodiments, the baseline 66 may be normalized with respect to front-end gain changes to mitigate the effects of device servoing. In some embodiments, the processor 50 may be configured to determine the efficacy of the CPR based at least in part on the one or more characteristics of the baseline.

Figure 5A:
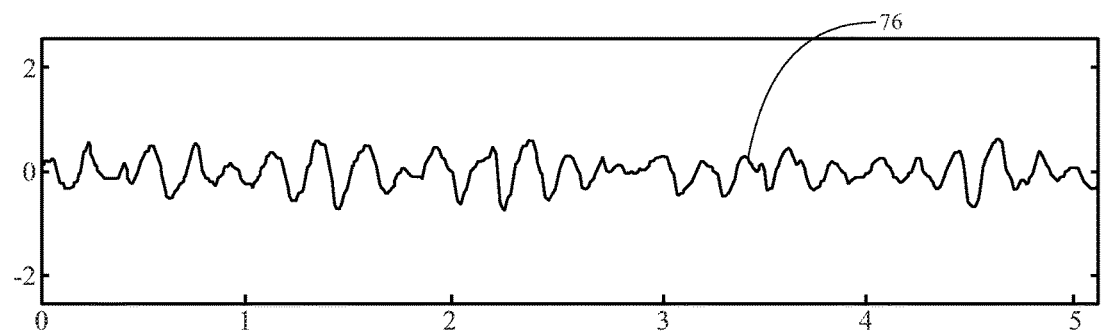
FIG. 5a is a graphical representation of an ECG signal having CPR artifact.
Figure 5B:
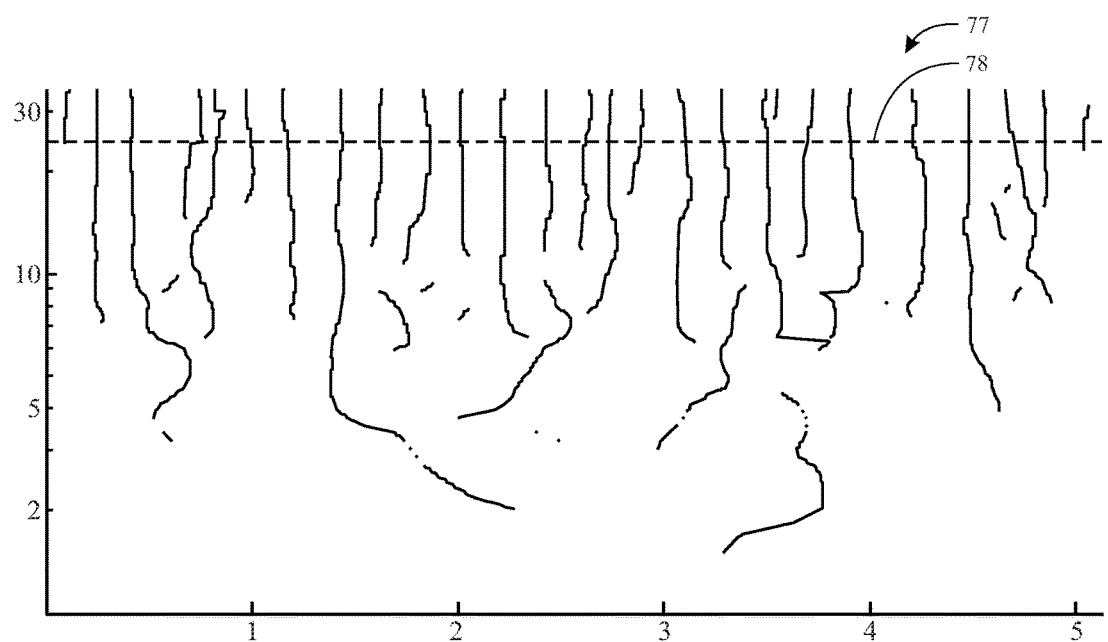

In certain embodiments, the processor 50 may be configured to determine the efficacy of CPR based at least in part on a characteristic measure related to the ECG signal (i.e., an ECPR metric) as disclosed in U.S. Pat. No. 8,983,588, which is hereby incorporated by reference in its entirety for all purposes. FIG. 5a is a graphical representation of an ECG signal 76, and FIG. 5b is a graphical representation of a modulus maxima scalogram 77 corresponding to the ECG signal 76 of FIG. 5a. The lines extending from top to bottom in the graphical representation of FIG. 5b indicate the location of the modulus maxima.

Figure 6:
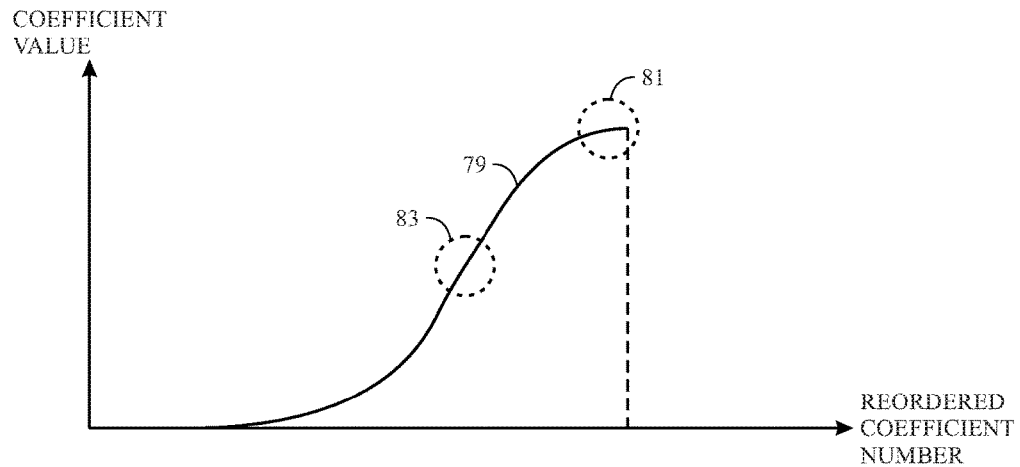
FIG. 6 is a graphical representation of a reordered coefficient curve that may be generated using coefficients obtained from a modulus maxima scalogram.

Artifacts due to CPR may be filtered out by identifying and removing the modulus maxima lines associated with the application of CPR. In some embodiments, the artifacts due to CPR may be filtered by using a CPR reference signal that correlates with CPR artifacts (e.g., comparing modulus maxima obtained from a CPR reference signal to the modulus maxima scalogram 77 and subtracting or removing modulus maxima lines corresponding to those in the CPR reference signal). In some embodiments, modulus maxima lines at short temporal scales may be selected. For example, modulus maxima values at a level 78 may be selected. The coefficients across the level 78 may be extracted and reordered from lowest to highest to form a reordered coefficient curve. An example of a reordered coefficient curve 79 is shown in FIG. 6. In some embodiments, regions without a modulus maxima line across the level 78 are set to zero to generate the reordered coefficient curve 79.

CPR may be characterized by high energy modulus maxima lines and coefficients corresponding to CPR may therefore be found at one region 81 (e.g., a CPR region) of the reordered coefficient curve 79. One or more other regions 83 (e.g., analysis region) remote from the CPR region 81 may be selected for analysis. A characteristic measure derived from the analysis region 83 may be indicative of the patient's underlying myocardial rhythm. The characteristic measure may include one or more of an amplitude of coefficients in the analysis region 83, a slope of the curve in the analysis region 83, and/or relative measures between the analysis region 83 and the CPR region 81. In some embodiments, the characteristic measure may be a value of a single coefficient at a position on the curve 79. In some embodiments, the characteristic measure may be a median, mode, or mean of values of several coefficients within a region (e.g., the analysis region 83) of the curve 79, for example. In some embodiments, the characteristic measure may include a temporal population statistic such as entropy, the standard deviation or other moment of distribution, or a value such as the maximum, minimum or mean value of the coefficients in the analysis region 83 of the curve 79, or the like.

Accordingly, in some embodiments, the processor 50 may be configured to receive the ECG signal from the ECG sensor 16, derive a time-scale transform surface of the ECG signal, and determine a characteristic measure using the time-scale transform surface, and determine an underlying myocardial rhythm based on a characteristic measure of the time-scale transform surface. As disclosed in U.S. Pat. No. 8,953,588 and as discussed above, the characteristic measure may be obtained in any of a variety of manners, including via manipulation of coefficients obtained from the ECG time-scale transform surface calculated over one or more surface scales. The characteristic measure may be monitored to detect changes in the underlying myocardial rhythm during CPR. Furthermore, the characteristic measure may be indicative of the efficacy of CPR. For example, an increase in the characteristic measure may reflect a positive response to CPR. Thus, the characteristic measure may be used by the processor 50 to assess the efficacy of CPR, as discussed in more detail below.

In certain embodiments, the processor 50 may be configured to determine a shock outcome prediction measure, such as a cardioversion outcome prediction (COP) metric as disclosed in U.S. Pat. Nos. 7,171,269 and 8,983,588, which are hereby incorporated by reference in their entirety for all purposes. The COP metric is a quantitative measure of the ECG signal and is generally indicative of the state of the myocardium and the likelihood that a defibrillation shock will be successful. For example, greater COP metric values indicate greater probability that a defibrillation shock will cause a return of spontaneous circulation (e.g., as compared to lower COP metric values indicating a lower probability that circulation will return after the shock).

The COP metric may be derived based on characteristics of the ECG signal. The wavelet transform of a signal x(t) is defined as $$T(a, b) = \frac{1}{\sqrt{a}} \int_{-\infty}^{+\infty} x(t) \varphi^* \left( \frac{t-b}{a} \right) dt \quad (1)$$

where $\varphi^*(t)$ is the complex conjugate of the wavelet function $\varphi(t)$, a is the dilation parameter of the wavelet, and b is the location parameter of the wavelet. The COP metric can be derived from a wavelet entropy-like measure computed over one or more of the scalogram scales and may be defined as:

$$WE_d = \frac{\int \ln |T(a'b)| db}{\int |T(a',b)| db}$$

where |T(a', b)| are the wavelet transform modulus values at a selected scale a'. All modulus values across the selected scale a' may be utilized. In some embodiments, the wavelet transform analysis employs a complex Morlet wavelet with a characteristic frequency between approximately 3 to 6 radians per second (rad/sec). In some embodiments, the characteristic frequency may be approximately 3, 3.5, 4, 4.5, 5, or 5.5 rad/sec. In some embodiments, the scale a' may correspond to a characteristic central frequency of the wavelet function of 45 Hertz (Hz), for example.

As noted above, the COP metric generally reflects the health of the myocardium and the probability of successful shock therapy. When the patient is in cardiac arrest, effective CPR may improve the health of the myocardium. Accordingly, monitoring the COP metric may provide an indication of whether the CPR is improving the health of the myocardium and/or effectively preparing the myocardium for a successful defibrillation shock. For example, an increase in the COP metric during CPR may indicate that the CPR has caused an increase in the probability of successful shock therapy and has advantageously prepared the heart for successful shock therapy, and thus, that the CPR is effective. Because the COP metric generally provides an indication of the health of the myocardium, an increase in the COP metric may indicate effective CPR across all rhythm types (e.g., asystole, ventricular fibrillation, pulseless electrical activity, and/or normal sinus rhythm). In some embodiments, the COP metric may be measured prior to and following CPR and may provide an indication of the efficacy of the CPR. In some embodiments, the COP metric may be measured continuously or periodically during CPR to detect the ongoing efficacy of CPR and to detect changes in the underlying myocardial rhythm during CPR.

Thus, as discussed above, the processor 50 of the monitor 14 may be configured to determine one or more first indicators based on the plethysmography signal received from the oximetry sensor 12 and/or one or more second indicators based on the ECG signal received from the ECG sensor 16. For example, the first indicator may include the amplitude of the non-cardiac pulses (i.e., the PCPR metric), the $rSO_2$, the $SpO_2$, the perfusion index, and/or one or more characteristics of the baseline determined from the plethysmography signal received from the oximetry sensor 12, and the second indicator may include a characteristic measure related to the ECG signal (i.e., the ECPR metric) and/or the COP metric based on the ECG signal received from the ECG sensor 16. In certain embodiments, the processor 50 of the monitor 14 may be configured to utilize one or more algorithms and/or classifiers (e.g., a trained classifier) to determine a combination metric (i.e., an MCPR metric) indicative of the efficacy of CPR based on one or more of the first and second indicators (e.g., the amplitude of the non-cardiac pulses, the $rSO_2$, the $SpO_2$, the perfusion index, the baseline, the characteristic measure related to the ECG signal, and/or the COP metric). In certain embodiments, the processor 50 of the monitor 14 may be configured to provide feedback (e.g., via the display 34 or the speaker 35) with respect to the CPR based at least in part on the MCPR metric.

Figure 7:
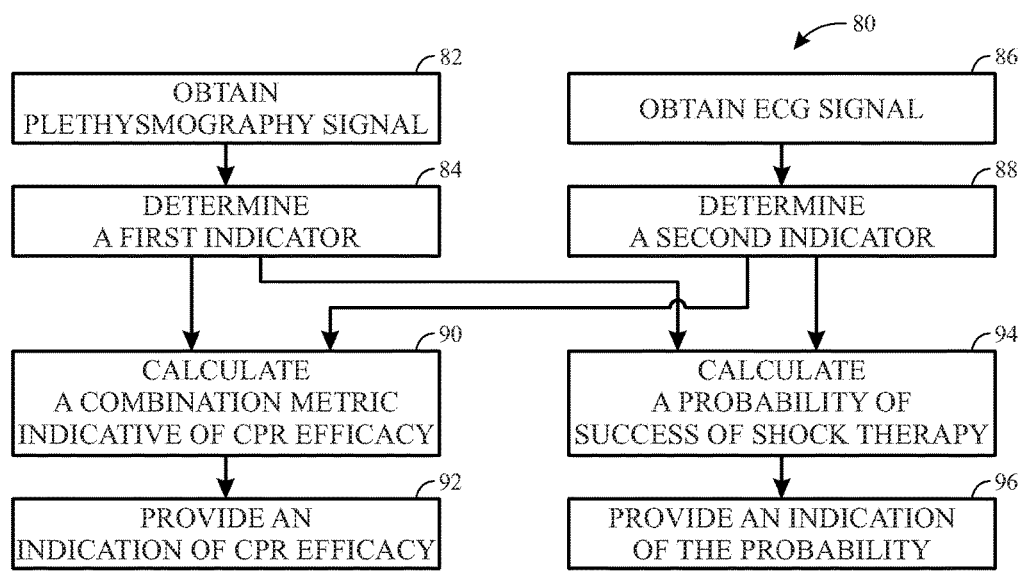
FIG. 7 is a process flow diagram of an embodiment of a method for determining an efficacy of cardiopulmonary resuscitation and a probability of success upon application of shock therapy using the medical monitoring system of FIG. 1.

FIG. 7 is a process flow diagram of an embodiment of a method 80 for using the system 10 to provide an output indicative of CPR efficacy and/or an output indicative of a probability of successful shock therapy. The methods disclosed herein include various steps represented by blocks. It should be noted the methods may be performed as an automated procedure by a system, such as the system 10. Although the flow charts illustrate the steps in a certain sequence, it should be understood that the steps may be performed in any suitable order and certain steps may be carried out simultaneously, where appropriate. Further, certain steps or portions of the methods may be performed by separate devices. For example, a first portion of each of the methods may be performed by the sensors 12, 16 while a second portion of the method may be performed by the monitor 14.

In step 82, the processor 50 of the monitor 14 may receive or obtain a plethysmography signal from a sensor, such as from the oximetry sensor 12. In step 84, the processor 50 may process the plethysmography signal to determine one or more first indicators related to CPR efficacy, such as the amplitude of non-cardiac pulses (e.g., the PCPR metric), the $SpO_2$, the $rSO_2$, the perfusion index, and/or one or more characteristics of the baseline using a plethysmography signal received from a sensor, such as the oximetry sensor 12.

In some embodiments, the processor 50 of the monitor 14 may also receive or obtain an ECG signal from the sensor 16, as shown in step 86. In step 88, the processor 50 may process the ECG signal to determine one or more second indicators related to CPR efficacy, such as a characteristic measures of the ECG signal (e.g., the ECPR metric) and/or the COP metric based on the ECG signal.

In step 90, the processor 50 of the monitor 14 may be configured to access and to utilize one or more algorithms and/or classifiers (e.g., a trained classifier) to determine a combination metric (i.e., an MCPR metric) indicative of the efficacy of CPR based on one or more of the first and/or second indicators (e.g., the amplitude of the non-cardiac pulses, the $rSO_2$, the $SpO_2$, the perfusion index, the baseline characteristics, the characteristic measure related to the ECG signal, and/or the COP metric). For example, in some embodiments, the amplitude of the non-cardiac pulses and the COP metric may be determined by the processor 50 and input into the classifier to output the MCPR metric. Although any suitable algorithm or classifier may be used, exemplary classifiers may include neural networks, genetic algorithms, probabilistic classifiers, or any combination thereof. The classifier may be trained based on any of a variety of input parameters or training data (e.g., sample data), such as the amplitude of the non-cardiac pulses, the $SpO_2$, the $rSO_2$, the perfusion index, the baseline characteristics, the characteristic measures of the ECG signal, the COP metric, and/or other indicators obtained from one or more patients that have undergone CPR.

Thus, one or more of the amplitude of the non-cardiac pulses, the $rSO_2$, the $SpO_2$, the perfusion index, the baseline characteristics, the characteristic measure related to the ECG signal, and/or the COP metric may be input into the algorithm or the classifier to output a classification indicative of the efficacy of CPR, such as the MCPR metric. In some embodiments, the processor 50 may be configured to weight the factors in any suitable manner during determination of the MCPR metric. For example, in some embodiments, a first weight may be applied to the $rSO_2$ and a second weight, lower than the first weight, may be applied to the $SpO_2$. In some embodiments, a highest weight may be applied to the COP metric during determination of the MCPR metric. For example, the weight applied to the COP metric may be greater than the weight applied to the other factors(s), such as the amplitude of the non-cardiac pulses, the $rSO_2$, the $SpO_2$, the perfusion index, the baseline characteristics, or the characteristic measure related to the ECG signal during determination of the MCPR metric. The MCPR metric may provide a more reliable and/or accurate indication of CPR efficacy than the individual factors.

In certain embodiments, the processor 50 of the monitor 14 may be configured to determine the CPR efficacy and to provide an indication of the CPR efficacy based at least in part on the MCPR metric, in step 92. In some embodiments, the processor 50 may be configured to monitor the MCPR over time (e.g., continuously or periodically) during CPR. In some embodiments, the processor 50 may compare the MCPR metric to a threshold value (e.g., a predetermined threshold value or an optimal range stored in the memory 48, which may be derived from historical and/or empirical patient data, for example) to determine if the MCPR metric is lower than the threshold value. In some embodiments, if the MCPR metric is above the threshold value, the processor 50 may determine that CPR is effective. In some embodiments, if the MCPR metric is below the threshold value, the processor 50 may determine that CPR is ineffective. Accordingly, the processor 50 may provide feedback (e.g., via the display 34 or the speaker 35) indicative of the efficacy of CPR based on comparison between the MCPR metric and the threshold value. For example, the processor 50 may provide a text message or an audible message that the CPR is effective or ineffective. In some embodiments, the processor 50 may provide (e.g., via the display 34 or the speaker 35) a color indicator and/or a numerical indicator indicative of the effectiveness of the CPR. In some embodiments, the processor 50 may generate, monitor, provide, and/or record a trend (e.g., a displayed trend line) of the MCPR metric over time. In some embodiments, the processor 50 may be configured to monitor and/or provide an indication of the relative CPR efficacy over time. For example, based on a trend of the MCPR metric during CPR, the processor 50 may be configured to determine and/or provide a relative indication of the efficacy of the CPR, such as an indication that the CPR efficacy is improving (e.g., if the MCPR increases) or not improving (e.g., if the MCPR decreases), thereby enabling the healthcare provider to identify whether certain changes in the CPR technique are effective for improving the efficacy of CPR.

In some embodiments, the processor 50 may additionally or alternatively be configured to provide (e.g., via the display 34 or the speaker 35) recommended adjustments for the administration of the CPR. For example, the processor 50, via the speaker 35 and/or display 34, may communicate to the person administering the CPR to adjust one or more components of the CPR (e.g., chest compressions and/or artificial respiration). For example, if $rSO_2$, the amplitude of the CPR pulses, and the COP metric are considered in calculating the MCPR metric, an MCPR metric below the threshold value may indicate that the brain of the patient is not receiving enough oxygen, that the chest compressions are not adequate, and/or that the patient's myocardium has not responded to the CPR. If $rSO_2$, the amplitude of the CPR pulses, and the COP metric are considered in calculating the MCPR metric, an MCPR metric that decreases during the application of CPR may indicate that the oxygen in the brain is decreasing, that the chest compressions are becoming weaker, and/or that the CPR is not improving the underlying rhythm of the patient's myocardium, for example. Accordingly, in such cases, the processor 50 may communicate to the person administering the CPR to increase the frequency and/or intensity of breaths administered during the CPR and/or the frequency and/or intensity of chest compressions based on the MCPR metric (e.g., based on whether the MCPR metric is lower than the threshold value and/or based on whether the MCPR metric is decreases during the CPR).

In some embodiments, the operator may select the desired indicators (e.g., inputs) for calculation of the MCPR metric using the user inputs 36. For example, in some embodiments, the operator may provide an input directing the processor 50 to consider a particular subset of the first and/or second indicators (e.g., a subset of the amplitude of the non-cardiac pulses, the $rSO_2$, the $SpO_2$, the perfusion index, the baseline characteristics, the characteristic measure related to the ECG signal, and/or the COP metric). In some embodiments, the operator may provide an input directing the processor 50 to apply particular respective weights to each of the factors. In some embodiments, the operator may input patient characteristics (e.g., age, size, weight, BMI, etc.), and the processor 50 may be configured to adjust or select the indicators, the weights, and/or the MCPR threshold value based on these patient characteristics, or may otherwise account for the patient characteristics in determining the MCPR metric. Alternatively, the processor 50 may detect the type of sensor that is in use (e.g. adult, pediatric, infant) and adjust the indicators, the weights, the MCPR threshold value, and/or the classifier based on these patient characteristics based on the patient population for the selected sensor. For example, if the amplitude of the non-cardiac pulses is considered in calculating the MCPR metric, the MCPR threshold value may be lower for younger patients (e.g., children) as compared with older patients (e.g., adults) because lower intensity chest compressions may be adequate for effective CPR.

Additionally or alternatively, in some embodiments, the processor 50 may use one or more of the first indicators and/or one or more of the second indicators to calculate a probability of success of shock therapy, as shown in step 94. As noted above, the perfusion index and/or the baseline characteristics may be generally indicative of blood flow at the monitoring site, which is expected to increase during effective CPR and/or as the health of the myocardium improves. For example, a low or decreasing gradient of the baseline during VF may indicate that the patient has been in VF for an extended period of time, and thus, may correspond to a reduced likelihood of success of the cardioversion shock. As such, the perfusion index, the baseline characteristics, and/or the COP metric may be used by the processor 50 to determine the probability of success upon application of shock therapy, for example. In particular, the characteristics (e.g., the percent change, the gradient, the amplitude) of the baseline, the perfusion index, and/or the COP metric may be input into an algorithm and/or a classifier (e.g., a trained classifier) to determine the probability of success of the shock therapy. The classifier may output a probability (e.g., a value from 0 to 1, a value from 0 to 100, or a value on any suitable scale) or a pass or fail indicator (e.g., the shock therapy is likely to be successful or likely to be unsuccessful).

Although any suitable algorithm or classifier may be used, exemplary classifiers may include neural networks, genetic algorithms, probabilistic classifiers, or any combination thereof. The classifier may be trained based on any of a variety of input parameters or training data (e.g., sample data), such as the perfusion index, the baseline characteristics, the COP metric, and/or other indicators obtained from one or more patients that have undergone CPR. In some embodiments, the processor 50 may be configured to determine and/or to utilize other indicators or factors, such the characteristic measure of the ECG signal, a downtime (e.g., a length of time since cessation of a normal sinus rhythm) based on the ECG signal, and/or a transition into VF (e.g., a length of time that the patient demonstrates an abnormal heart rhythm, such as a tachycardia, prior to entering VF) based on the ECG signal, and the processor 50 may utilize such additional factors to determine the probability of successful shock therapy. For example, a longer downtime (e.g., exceeding a predetermined period of time) and/or a longer period of abnormal heart rhythm prior to VF may reduce the probability of successful shock therapy. In some embodiments, the processor 50 may compare the probability of successful shock therapy to a threshold value (e.g., a predetermined threshold value or a shock threshold value) to determine whether the operator should apply a defibrillation shock to the patient. For example, if the probability exceeds the threshold value, the processor 50 may determine that application of a defibrillation shock is medically appropriate and should be applied.

In some embodiments, the processor 50 may be configured to weight the indicators or factors in any suitable manner during determination of the probability of successful shock therapy. For example, in some embodiments, the weight applied to the COP metric may be greater than the weight applied to the other factors(s), such as the perfusion index and/or the baseline characteristics during determination of the probability of successful shock therapy. In some embodiments, the algorithm or classifier used to determine the probability of success of a cardioversion shock in step 94 may be updated based on data received by the processor 50. For example, if an unsuccessful shock is detected or identified by the processor 50, the processor 50 may update the classifier to classify the state of the myocardium at the time of the unsuccessful shock as inadequate (e.g., not shockable). In some embodiments, following an unsuccessful shock, the processor 50 may update the classifier by increasing the threshold value (e.g., so that the processor 50 may determine the probability and/or instruct the operator to apply a defibrillation shock only if the probability of successful shock therapy is higher than at the time of the previous unsuccessful shock). Thus, an unsuccessful shock may cause or initiate a change in the classifier. In some embodiments, patient data obtained prior to the unsuccessful shock (e.g., signals obtained from the sensors 12, 16 may be discarded and/or not utilized in calculating the probability of successful shock therapy.

In step 96, the processor 50 may provide an indication of the probability. For example, the processor 50 may provide an indication of the probability of success and/or notify the CPR (e.g., via the display 34 or the speaker 35) provider when a shockable myocardial rhythm is detected (e.g., when the probability exceeds a threshold value, such as a predetermined threshold value or percentage stored in the memory 48, such as 0.5, 0.6, 0.7, 0.8, 0.9, 0.95 more, which may be determined based on historical or empirical data). Such notifications may reduce the number of unsuccessful defibrillation shocks and customizing resuscitation efforts for the patient. It should be noted that the processor 50 may be configured to provide feedback related to the efficacy of the CPR to enable the healthcare provider to apply CPR in a manner that improves the health of the myocardium and prepares the myocardium for a defibrillation shock, as shown in step 92, and to notify the healthcare provider to apply the defibrillation shock upon detection of a shockable rhythm, as shown in step 96.

In some embodiments, the processor 50 may be configured to monitor the probability of successful shock therapy over time (e.g., continuously or periodically) during CPR. In some embodiments, the processor 50 may compare the probability to the threshold value. In some embodiments, if the probability is above the threshold value, the processor 50 may provide instructions (e.g., via the display 34 or the speaker 35) to apply a defibrillation shock. In some embodiments, if the probability is below the threshold value, the processor 50 may provide instructions to continue CPR and/or provide feedback related to the efficacy of CPR. In some embodiments, the processor 50 may provide a visual text message or an audible message or sound (e.g., a beep of a particular pitch or tone, a buzzer, or the like) indicating that the shock therapy should be applied. In some embodiments, the processor 50 may provide (e.g., via the display 34 or the speaker 35) an indicator of the probability of successful shock therapy (e.g., a numerical indicator indicative of the probability, a color, a word, or the like). In some embodiments, the processor 50 may generate, record, and/or provide a trend (e.g., a displayed trend line) of the probability of successful shock therapy over time to enable the operator to monitor whether the patient's myocardium is approaching a state in which shock therapy may be appropriate. Display of the trend line may enable the operator to prepare the appropriate medical equipment and/or to assume proper body positioning for application of the defibrillation shock when the trend demonstrates that the patient's myocardium is approaching a state in which shock therapy may be appropriate, for example.

In some embodiments, the operator may select the desired indicators (e.g., inputs) for calculation of the probability of successful shock therapy using the user inputs 36. For example, in some embodiments, the operator may provide an input directing the processor 50 to consider a particular subset of the first and/or second indicators (e.g., a subset of the perfusion index, the baseline characteristics, and/or the COP metric). In some embodiments, the operator may provide an input directing the processor 50 to apply particular respective weights to each of the indicators. In some embodiments, the operator may input patient characteristics (e.g., age, gender, size, weight, BMI, etc.), and the processor 50 may be configured to adjust or select the indicators, the weights, and/or the threshold value based on these patient characteristics, or may otherwise account for the patient characteristics in determining the probability. Alternatively, the processor 50 may detect the type of sensor that is in use (e.g. adult, pediatric, infant) from an encoder of the sensor 12, 16 and adjust the indicators, the weights, the threshold value, and/or the classifier based on these patient characteristics based on the patient population for the selected sensor. For example, the threshold value may be lower for younger patients (e.g., children) as compared with older patients (e.g., adults) because the myocardium of younger patients may respond differently to shock therapy.

Figure 8:
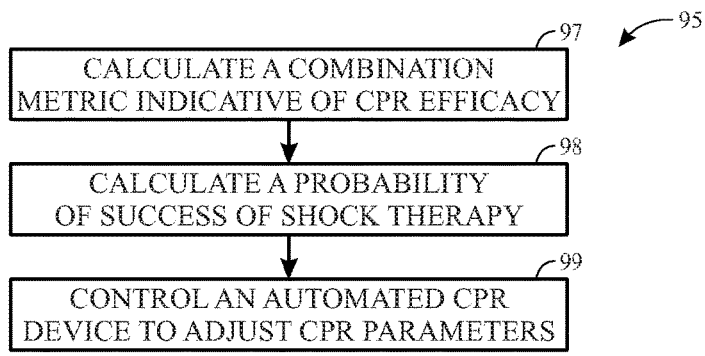
FIG. 8 is a process flow diagram of an embodiment of a method for controlling an automated CPR device based on a determination of CPR efficacy.

In some embodiments, the system 10 may include or be configured for use with an automated CPR device configured to apply compressions to the patient's chest. FIG. 8 is a process flow diagram of an embodiment of a method 95 for controlling the automated CPR device based on the MCPR metric and/or based on the probability of success of shock therapy. In step 97, the processor 50 may determine the MCPR metric, as discussed above. In step 98, the processor 50 may determine the probability of success of shock therapy, as discussed above. In step 99, the processor 50 may cause adjustment of CPR parameters (e.g., rate and/or depth of chest compressions) applied by the automated CPR device based on the MCPR metric and/or the probability of successful defibrillation shock. For example, the processor 50 may cause the automated CPR device to increase a depth and/or a frequency of chest compressions if the MCPR metric is below the MCPR threshold and/or decreases over a period of time during application of CPR. In some embodiments, the processor 50 may cause cessation of chest compressions by the automated CPR device and may initiate a defibrillation shock by the automated CPR device when the probability of successful defibrillation exceeds the threshold.

Figure 9:
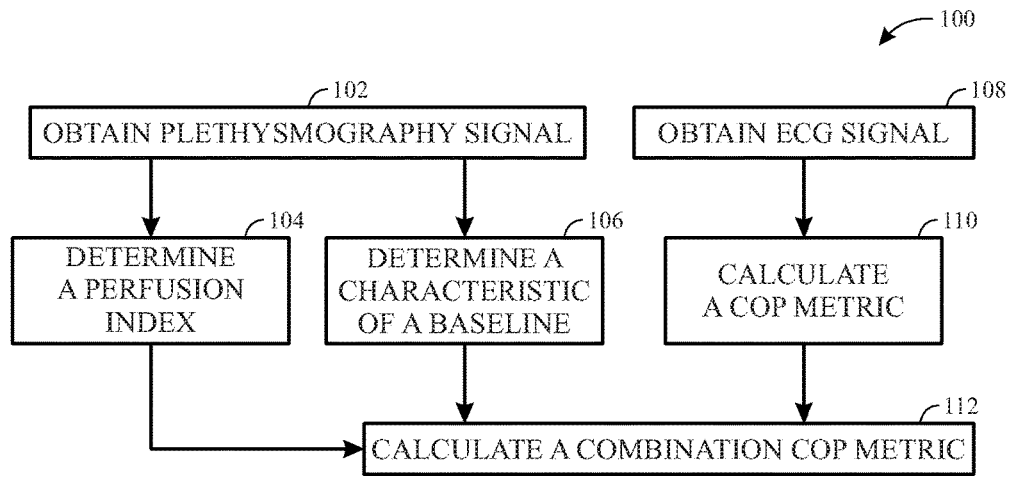
FIG. 9 is a process flow diagram of an embodiment of a method for determining an improved cardioversion outcome prediction (COP) metric using the medical monitoring system of FIG. 1.

FIG. 9 is a process flow diagram of an embodiment of a method 100 for using the system 10 to determine a combination COP metric based at least in part on a perfusion index and/or a baseline of a plethysmography signal. In step 102, the processor 50 of the monitor 14 may receive or obtain a plethysmography signal from the oximetry sensor 12. In step 104, the processor 50 may process the plethysmography signal to determine the perfusion index. In step 106, the processor 50 may process the plethysmography signal to determine one or more characteristics of a baseline of the plethysmography signal.

As shown in step 108, the processor 50 of the monitor 14 may also receive or obtain an ECG signal from the sensor 16. In step 110, the processor 50 may process the ECG signal to determine the COP metric based on the ECG signal. In step 112, the processor 50 of the monitor 14 may be configured to calculate a combination COP metric based on the COP metric in combination with one or both of the perfusion index or the baseline characteristics. For example, the processor 50 may access and utilize one or more algorithms and/or classifiers (e.g., a trained classifier) to determine the combination COP metric based on the COP metric, the perfusion index, and/or the baseline characteristics. In some embodiments, the COP metric may be adjusted based on the perfusion index and/or the baseline characteristics (e.g., to generate the combination COP metric). For example, if the perfusion index increases or is above a predetermined perfusion index threshold, the COP metric may be adjusted upwardly to generate an increased combination COP metric (e.g., higher than the COP metric) indicative of the probability of successful shock therapy.

The processor 50 may be configured to weight the COP metric, the perfusion index, and/or the baseline characteristics in any suitable manner during determination of the combination COP metric. For example, in some embodiments, a first weight may be applied to the COP metric and a second weight, lower than the first weight, may be applied to the perfusion index. In some embodiments, a highest weight may be applied to the COP metric. For example, the weight applied to the COP metric may be greater than the weight applied to the other indicator(s), such as the perfusion index or the characteristics of the baseline during determination of the likelihood of success of the cardioversion shock.

Because the combination COP metric considers multiple factors that are each indicative of the state of the myocardium, the combination COP metric may provide a more reliable indicator of the prediction of success of shock therapy, as compared with the COP metric calculated via Equation 2. In some embodiments, the second indicator may include the combination COP metric. Thus, the combination COP metric may be calculated in step 88 of the method 80 of FIG. 7 (e.g., in lieu of the COP metric), and the combination COP metric may be utilized in step 86 to calculate the MCPR metric and/or in step 94 to calculate the probability of success of shock therapy.

Figure 10:
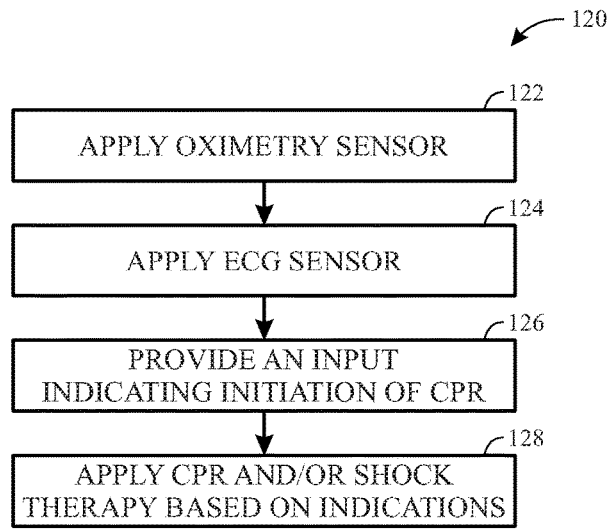
FIG. 10 is a process flow diagram of an embodiment of a method of using the medical monitoring system of FIG. 1 to administer CPR.

FIG. 10 is a process flow diagram of a method 120 of using the system 10 to administer CPR. In step 122, the oximetry sensor 12 may be applied to the patient's tissue. In step 124, the ECG sensor 16 may be applied to the patient's tissue. In step 126, an operator may provide a user input (e.g., via input 36, which may be a touchscreen or any other suitable input device) indicating initiation of CPR application. In step 128, the operator may provide CPR (e.g., chest compressions and/or breaths) and/or apply shock therapy based on indications (e.g., displayed or audible indications) provided by processor 50, which may be generated and provided as discussed above with respect to FIG. 7. For example, if the processor 50 provides an indication to increase a depth of chest compressions (i.e., because the MCPR metric is below the MCPR threshold), the operator may increase the depth of chest compressions. If the processor 50 provides an indication to apply shock therapy, the operator may cease chest compressions and apply a defibrillation shock.

What is claimed is:

1. A method for determining an efficacy of cardiopulmonary resuscitation (CPR), the method comprising, using a processor configured to determine the efficacy of CPR, wherein the processor is associated with a patient monitor, an oximetry sensor, and an electrocardiogram (ECG) sensor, and wherein determining the efficacy of CPR comprises:

receiving, at the processor, a plethysmography signal from the oximetry sensor;
receiving, at the processor, an ECG signal from the ECG sensor;
determining a first indicator related to the efficacy of CPR based on the plethysmography signal, using the processor;
determining a second indicator related to the efficacy of CPR based on the ECG signal, using the processor;
combining the first indicator and the second indicator to determine a combination metric indicative of the efficacy of CPR, using the processor; and
adjusting parameters controlling one or both of a rate or depth of compressions applied by a CPR device based on the combination metric.

2. The method of claim 1, wherein the first indicator comprises an amplitude of a non-cardiac pulse, an oxygen saturation ($SpO_2$), a regional oxygen saturation ($rSO_2$), a perfusion index, a characteristic of a baseline of the plethysmography signal, or any combination thereof, and wherein the second indicator comprises a characteristic measure of the ECG signal, a cardioversion outcome prediction (COP) metric, or any combination thereof.

3. The method of claim 1, wherein the first indicator comprises an amplitude of a non-cardiac pulse and wherein the second indicator comprises a characteristic measure of the ECG signal, a cardioversion outcome prediction (COP) metric.

4. The method of claim 3, wherein combining the first and second indicators comprises assigning weights to the first and second indicators, and wherein the COP metric is assigned a higher weight than the amplitude of the non-cardiac pulse.

5. The method of claim 1, comprising determining, using the processor, an indication of the efficacy of CPR based on the combination metric, and providing, using the processor, the indication of the efficacy of CPR on a display or via a speaker.

6. The method of claim 1, comprising determining a probability of a return of spontaneous circulation upon application of a defibrillation shock, wherein determining the probability comprises:

determining a combination cardioversion outcome prediction (COP) metric indicative of the probability based at least in part on a perfusion index derived from the plethysmography signal and a COP metric derived from the ECG signal, using the processor; and
providing, using the processor, an indication of the probability on a display or via a speaker.

7. The method of claim 1, wherein the adjusting comprises increasing a depth or frequency of the compressions responsive to the combination metric being below a threshold.

8. The method of claim 1, wherein the adjusting comprises increasing a depth or frequency of the compressions responsive to the combination metric decreasing over time.

9. A system, comprising:
a processor associated with an oximetry sensor and an electrocardiogram (ECG) sensor, or with a patient monitor that is configured to be communicatively coupled to the oximetry sensor and the ECG sensor, wherein the processor is configured to execute instructions stored on a memory to:
determine a first indicator related to an efficacy of CPR based on a plethysmography signal generated by the oximetry sensor;

determine a second indicator related to the efficacy of CPR based on an ECG signal generated by the ECG sensor;

input the first indicator and the second indicator into a trained classifier to output a metric indicative of an efficacy of CPR;

output an indication of the efficacy of CPR based on the metric on a display or via a speaker of the patient monitor, the oximetry sensor, or the ECG sensor; and determine a probability of a return of spontaneous circulation upon application of a defibrillation shock by determining a combination cardioversion outcome prediction (COP) metric indicative of the probability based at least in part on a perfusion index derived from the plethysmography signal and a COP metric derived from the ECG signal; and provide an indication of the probability on a display or via a speaker, wherein the indication of the probability comprises a displayed or an audible message instructing an operator to apply the defibrillation shock responsive to a determination that the combination COP metric exceeds a threshold value.

10. The system of claim 9, wherein the first indicator comprises an amplitude of a non-cardiac pulse of the plethysmography signal, a regional oxygen saturation (rSO$_2$) value, an oxygen saturation value (SpO$_2$), a perfusion index, a baseline of the plethysmography signal, or any combination thereof.

11. The system of claim 9, wherein the second indicator comprises a characteristic measure of the ECG signal or a cardioversion outcome prediction (COP) metric.

12. The system of claim 9, wherein the first indicator comprises an amplitude of a non-cardiac pulse of the plethysmography signal and the second indicator comprises at least one of a characteristic measure of the ECG signal or a cardioversion outcome prediction (COP) metric.

13. The system of claim 9, wherein the second indicator comprises a cardioversion outcome prediction (COP) metric, and the processor is configured to assign a first weight to the COP metric and a second weight to the first indicator during determination of the efficacy of CPR, and the first weight is greater than the second weight.

14. The system of claim 9, wherein the trained classifier comprises a neural network.

15. A system, comprising:
an oximetry sensor configured to be applied to a patient and to generate a plethysmography signal;
an electrocardiogram (ECG) sensor configured to be applied to the patient and to generate an ECG signal;
a processor associated with the oximetry sensor and the ECG sensor, or with a patient monitor that is configured to be communicatively coupled to the oximetry sensor and the ECG sensor, wherein the processor is configured to execute instructions stored on a memory to:
determine a first indicator based on the plethysmography signal;
determine a second indicator based on the ECG signal;
determine an efficacy of CPR based at least in part on the first indicator and the second indicator; and
provide an indication of the efficacy of CPR on a display or via a speaker until the probability exceeds a threshold value, and to provide instructions on the display or via the speaker to stop CPR and apply a defibrillation shock if the probability exceeds the threshold value.

16. The system of claim 15, wherein the first indicator comprises an amplitude of a non-cardiac pulse, an oxygen saturation (SpO$_2$), a regional oxygen saturation (rSO$_2$), a perfusion index, a characteristic of a baseline of the plethysmography signal, or any combination thereof, and wherein the second indicator comprises a characteristic measure of the ECG signal, a cardioversion outcome prediction (COP) metric, or any combination thereof.

17. The system of claim 15, wherein the processor is configured to provide an indication of the efficacy of CPR on a display or via a speaker.

18. The system of claim 17, wherein the processor is configured to provide an audible indication, and wherein a characteristic of the audible indication varies based on the efficacy of the CPR.

19. The system of claim 15, wherein the processor is configured to determine a probability of a return of spontaneous circulation upon application of shock therapy based at least in part on the first indicator and the second indicator.

* * * * *